United States Patent
Marc et al.

(10) Patent No.: US 7,993,923 B2
(45) Date of Patent: Aug. 9, 2011

(54) PEPTIDE FRACTIONS PROMOTING GROWTH AND SYNTHESIS OF DESIRED PRODUCT(S) INTO CELL AND/OR TISSUE CULTURE

(75) Inventors: Annie Marc, Seichamps (FR); Jean-Louis Goergen, Domevre en Haye (FR); Bérangère Farges-Haddani, Beaumont (FR)

(73) Assignees: Pierre Fabre Medicament, Boulogne-Billancourt (FR); Centre National de la Recherche Scientifique (CNRS), Paris (FR)

( * ) Notice: Subject to any disclaimer, the term of this patent is extended or adjusted under 35 U.S.C. 154(b) by 965 days.

(21) Appl. No.: 11/792,953

(22) PCT Filed: Dec. 14, 2005

(86) PCT No.: PCT/EP2005/056782
§ 371 (c)(1),
(2), (4) Date: Aug. 29, 2007

(87) PCT Pub. No.: WO2006/064020
PCT Pub. Date: Jun. 22, 2006

(65) Prior Publication Data
US 2009/0124010 A1    May 14, 2009

(30) Foreign Application Priority Data
Dec. 14, 2004  (FR) ..................................... 04 13250

(51) Int. Cl.
*C12N 5/07*   (2010.01)
*C12N 5/00*   (2010.01)
(52) U.S. Cl. ........................................ 435/404; 435/325
(58) Field of Classification Search ........................ None
See application file for complete search history.

(56) References Cited

FOREIGN PATENT DOCUMENTS

| WO | WO-96/26266 A | 8/1996 |
|---|---|---|
| WO | WO-99/57246 A | 11/1999 |
| WO | WO-01/23527 A | 4/2001 |
| WO | WO-03/045995 A | 6/2003 |

OTHER PUBLICATIONS

Deparis et al., "Promoting effect of rapeseed proteins and peptides on Sf9 insect cell growth", Cytotechnology, 2003, vol. 42, pp. 75-85.*
Philipchuk et al. "Rapeseed oil meal as a nitrogenous substrate for microbial fermentation". Journal of General and Applied Microbiology. 1979, vol. 25, pp. 117-125.*
Vioque et al. "Production and characterization of an extensive rapeseed protein hydrolysate", JAOCS, 1999, vol. 76, No. 7, pp. 819-823.*
Hugli et al., Journal of Biological Chemistry, vol. 247, No. 9, May 10, 1972, pp. 2828-2834.
Burteau et al., "Fortification of a protein free cell culture medium with plant peptones improves the cultivation and productivity of an interferon gamma CHO cell line," in Vitro Cell Dev. Biol., vol. 39, Jul. 2003, pp. 291-296.
Franek et al., "Plant protein hydrolysates: Preparation of defined peptide fractions promoting growth and production in animal cells cultures," Biotechnol. Prog., vol. 16, 2000, pp. 688-692.
Heidemann et al., "The use of peptones as medium additives for the production of a recombinant therapeutic protein in high density perfusion cultures of mammalian cells," Cytotechnology, Kluwer Academic Publishers, vol. 32, 2000, pp. 157-167.
"Quest International Product Information," 1998, XP002156903.

* cited by examiner

*Primary Examiner* — Vera Afremova
(74) *Attorney, Agent, or Firm* — Birch, Stewart, Kolasch & Birch, LLP

(57) ABSTRACT

The invention relates to preparing and/or supplementing a cell or tissue culture medium. In particular, said invention relates to a serum-free and/or protein-free cell culture medium comprising peptide fractions isolated from rapeseeds, in particular rapeseeds cakes. A method for the production of a cell culture comprising said peptide fractions and for the use thereof is also disclosed.

7 Claims, 7 Drawing Sheets

PEPTIDE FRACTIONS PROMOTING GROWTH AND SYNTHESIS OF DESIRED PRODUCT(S) INTO CELL AND/OR TISSUE CULTURE

The present invention relates to the field of supplementing of cell or tissue culture media. More particularly, the present invention relates to a serum-free and/or protein-free cell culture medium comprising peptide fractions isolated from rapeseeds, in particular rapeseed cakes. The invention also relates to a method of cell culture comprising these peptide fractions and also to the use thereof.

Since the existence of live cells became known, cell culture types and techniques have not ceased to increase and to diversify.

Initially, cell cultures used undefined media such as plasma, serum or embryonic extracts. It wasn't until the mid-1950s that the first defined culture medium emerged, said medium comprising, in addition to salts and glucose, various amino acids and vitamins that the cells could not synthesize.

More recently, it has been shown that, among all the amino acids provided, L-glutamine plays an essential role both as a source of energy and as a source of carbon and nitrogen, mainly for allowing purine and pyrimidine synthesis. However, a first drawback lies in the fact that glutamine is not stable in free amino acid form and will have a tendency to decompose to ammonium ions and pyroglutamic acid. A solution to this problem, based on the use of cereal hydrolyzates, has been provided by patent application WO 96/26266 filed in the name of QUEST INTERNATIONAL.

In general, cells and tissues, and more particularly animal cells, are cultured in vitro in a nutritional medium, called base or basal medium, supplemented with 5 to 20% of serum, generally fetal calf serum or FCS.

However, the use of such sera has other drawbacks, such as i) the introduction of animal proteins that must subsequently be eliminated, ii) the potential introduction of contaminants such as fungi, bacteria, viruses or prions, and iii) a variable quality and high costs.

In addition, in order to limit more particularly the risks of bovine spongiform encephalopathy (BSE) in pharmaceutical products, both national legislation and international legislation anticipate that the use of products of animal origin will be prohibited in the near future.

Among these drawbacks, the risk of introducing contaminants remains the most problematic and has prompted the use of serum-free medium or SFM. However, certain SFMs used today still contain peptones and hydrolyzates derived from animals and are not therefore entirely satisfactory in terms of the contamination risks defined above.

As regards SFMs devoid of material of animal origin, they are generally derived from protein-rich starting materials such as, for example, cereal starting materials, for instance rice (WO 98/15614; WO 99/57246) or wheat. By way of example of other starting materials used, mention may also be made of soybean (WO 01/23527; WO 00/03000), or else cucumber (WO 99/47648). However, such culture media are relatively costly to obtain and are generally derived from starting materials with a high protein potential that can be used for other applications such as, for example, food applications. There exists therefore a real need to develop culture media that are completely devoid of animal-derived products and inexpensive or, at the very least, derived from a starting material whose value is and/or can be only slightly exploited.

The present invention proposes to overcome this shortcoming of the prior art by proposing a culture medium devoid of serum and obtained from a plant starting material with a low initial protein content.

More particularly, the present invention relates to the use of a peptide extract for preparing and/or supplementing a serum-free in vitro cell or tissue culture medium, said extract being obtained by successive fractionations of a plant starting material, characterized in that said plant starting material consists of rapeseed.

The term "serum-free medium" should be understood to mean a medium devoid of serum of animal origin, such as FCS, FBS (fetal bovine serum) or any analogous serum.

Today, most products derived from cell culture are monoclonal antibodies, viruses and recombinant proteins. From an industrial point of view, the cells most widely cultured today, besides cells from tissues or as a replacement for animal models in toxicology, are hybridomas, VERO cells (African green monkey kidney cells), BHK cells (baby hamster kidney), CHO cells (Chinese hamster ovary), NS0 cells, or *Spodoptera frugiperda* (Sf9) cells infected with a baculovirus. Hybridomas are monoclonal antibody-producing cells, whereas VERO and CHO cells are generally used for the production of viruses or else of recombinant proteins. Of course, this listing is in no way limiting and the present invention may relate to cells of any type.

By way of nonlimiting examples, mention may also be made of the following tissues: cartilage, muscle cells, skin, bone cells, tendons, embryonic cells, artificial organs.

A first characteristic of the invention is based on the very use of oil-yielding plants, and most particularly of rapeseed. In fact, unlike the cereals or other starting materials used to date, this seed is particularly rich in lipids and low in proteins. For these reasons, those skilled in the art have not, to date, sought to use rapeseed for the preparation of culture media since it was accepted that, for this purpose, it was necessary to preferentially use protein-rich starting materials.

Entirely surprisingly, and contrary to the bias of the prior art, it has been demonstrated that it is possible to use rapeseed for preparing serum-free and/or protein-free culture media. Even more surprisingly, it has also been demonstrated that such media comprising peptide extracts derived from rapeseed make it possible not only to obtain a significant increase in the final concentration of the cells or tissues placed in culture, but also an increase in the specific rate of production of one or more molecules of interest by cells in culture.

Furthermore, the fact that such an increase in the final cell or tissue concentration is not linked solely to a nutritional effect has also been demonstrated.

According to a preferred aspect, the present invention relates to the use of an extract as described above, characterized in that said peptide extract performs a function in terms of increasing the cell or tissue concentration and/or in terms of increasing the lifespan of the cells and/or in terms of the specific rate of production of one or more molecules of interest, said function being bound not solely by the elemental amino acid composition, but by the composition, of said amino acids, in peptide form.

This particularly positive effect was established in comparison with the effect caused by a medium of elemental composition, i.e. consisting of free amino acids, identical in all respects to the composition of the peptide extract that is the subject of the invention, except for the fact that, in the extract according to the invention, the amino acids are in peptide form. This point will be established more clearly in the light of the examples hereinafter.

In general, it emerges from the prior art that the culture media used to date have been prepared with the aim of providing the cells or tissues with nutrients, and especially amino acids, required by the cell as a source of energy and as a source of carbon and nitrogen. These amino acids are generally present in the culture media in mainly free amino acid form. Some amino acids are present in dipeptide or tripeptide form in order to give them sufficient stability in a liquid medium (WO 96/26266).

The present invention shows, entirely surprisingly, that the peptide extract that is the subject of the invention and is obtained by successive fractionations of a starting material derived from rapeseed, performs a function that promotes growth of the cells or tissues in culture and helps keep them alive. In fact, as will emerge more clearly from the examples described hereinafter, it has been shown that, for the same amounts of each amino acid, it is necessary for the latter to be in the form of peptides in order for an increase in the concentration, and more particularly an increase in the lifespan of the cells or tissues and in the specific rate of production of one or more molecules of interest, to be observed. It appears that the invention is based not only on amounts of free amino acids, but on a given composition of peptides, preferably di-, tri-, tetra- or pentapeptides.

Without wishing to be bound by any theory, it would seem to be probable that the extract that is the subject of the present invention does not solely play a positive role on growth, but also has a role in terms of reducing the induction of apoptosis.

According to another aspect, the present invention relates to the use of a peptide extract for preparing and/or supplementing a protein-free in vitro cell or tissue culture medium, said extract being obtained by successive fractionations of a plant starting material, characterized in that said plant starting material consists of rapeseed.

In a manner similar to the serum-free medium described above, the use of the peptide extract as described above is characterized in that said peptide extract performs a function in terms of increasing the cell or tissue concentration and/or in terms of increasing the lifespan of the cells and/or in terms of the specific rate of production of one or more molecules of interest, said function being bound not only by the elemental amino acid composition, but by the composition, of said amino acids, in peptide form.

The expression "protein-free" should not be understood to mean a medium completely devoid of proteins, but a medium completely devoid of protein of animal origin. This expression encompasses, inter alia, the names ADCF (animal derived component free) or alternatively "animal protein free".

In fact, the presence of proteins is generally necessary for the growth of cells or tissues. The important point, as mentioned above, lies in the absence of protein of animal origin. Such a culture medium makes it possible to eliminate, even more radically than serum-free media, any risk of contamination by a molecule, or part of such a molecule, that would be of animal origin.

According to a preferred embodiment, the invention is directed toward the use as described above, said use being characterized in that the plant starting material consists of rapeseed cake.

The term "cake" should be understood to mean the solid residue obtained when oil-yielding seeds and fruit are treated for the purpose of extracting oil (definition in the Petit Larousse Illustré, 1989, page 975). One advantage of the present invention therefore lies in the low cost of the starting material used. In fact, cakes constitute, in all oil-yielding crops, the coproducts obtained, and not given much worth to date, by the oil industry. The present invention therefore provides an approach for recovering and increasing the value of oil industry waste.

Figure 1:
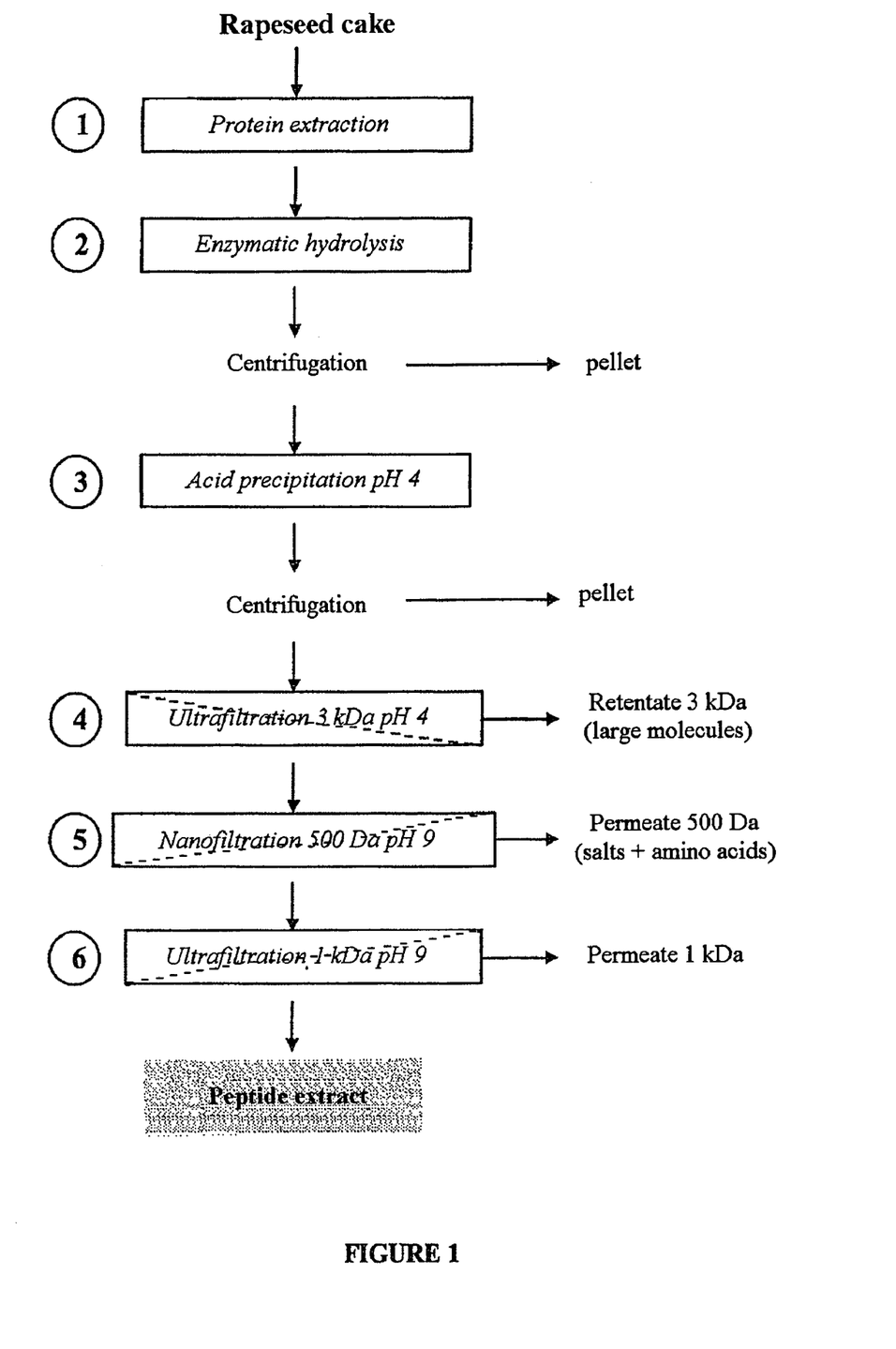
FIG. 1 represents a flowsheet of an embodiment of a method for obtaining the peptide extract in accordance with the invention.

The peptide extracts that are the subject of the present invention are preferably obtained by hydrolysis of rapeseed cakes. A fractionation process for obtaining such extracts has been developed. FIG. 1 represents a flowsheet diagram of a preferred process. Of course, any modification, that is obvious to those skilled in the art, of this process, is part of the present invention.

More particularly, this process comprises six successive steps corresponding respectively to:

Step 1: Protein Extraction

The objective of this step is the production of a concentrate of rapeseed proteins, in order to have a starting material enriched in rapeseed proteins (70-80% of protein material relative to solids, against 30-40% in the rapeseed cake).

Step 2: Hydrolysis

The aim of this step is to hydrolyze the proteins in order to obtain a solution consisting of peptides.

Here also, the process used is conventional. The use of Alcalase®, which is an enzyme preparation of microbial origin, consequently has no risk of transmission of biological elements of animal origin (viruses that are pathogenic against animal cells, prions, etc.). Hydrolysis time: 5 hours, T°=60° C., pH=9, enzyme concentration/substrate concentration ratio=1/10. Free amino acid content of the hydrolyzate: 4% by mass.

Step 3: Acid Precipitation, pH 4

This step is aimed at eliminating the "large" molecules, essentially large proteins and peptides, present in the hydrolyzate, thereby making it possible to reduce clogging during the subsequent filtration steps.

Step 4: Ultrafiltration with a Membrane Having a Cutoff Threshold of 3 kDa

The objective of this step is to recover the small peptides by elimination of the molecules greater than 3000 Da in size (phenolic compounds such as tannins and polypeptides). The process used is a conventional membrane process for enriching in small peptides contained in a hydrolyzate.

Step 5: Nanofiltration with a Membrane Having a Cutoff Threshold of 500 Da

The aim is to reduce the amount of free amino acids in the small-peptide solution obtained after step 4 and to desalify this same solution in order to reduce the osmolarity of the mixture. A conventional desalification process is used. An 80% reduction in salt concentration allows better fractionation of the peptides according to their charge in step 5.

Step 6: Ultrafiltration with a Membrane Having a Cutoff Threshold of 1 kDa

This step involves fractionating the small peptides according to their size and their charge.

This step is particularly advantageous in the sense that it is based on the use of an ultrafiltration membrane for the purpose of fractionating, according to their size and their charge, the peptides contained in a plant hydrolyzate. Compared with the permeate, the final retentate, corresponding to the peptide extract according to the invention, has a higher content of peptides containing acidic amino acids, and a lower content of peptides containing basic amino acids.

It should be noted that the process described above is given only by way of illustration of one embodiment, but is in no way limiting. Any modification or improvement in the latter should be considered to be part of the present invention.

In order to more thoroughly characterize the peptide extracts, that are the subject of the present invention, several studies and assays have been carried out, the detailed protocols and results of which are presented later on in the examples. However, it emerges that the peptide extract used in the context of the invention is characterized in that it consists of at least 80%, preferably at least 90%, by mass of nitrogenous material.

The expression "nitrogenous material" is intended to denote, in the present description, any material consisting of amino acids, it being possible for the latter to be in free form or associated as peptides or proteins.

Such a concentration of nitrogenous material, from an oil-yielding plant with a low protein content, and more particularly rapeseed, is obtained by means of the process described above. This characteristic is very advantageous in the sense that most plant extracts for supplementing a culture medium have much lower contents of nitrogenous material. By way of example, the cereal-derived extracts described in the patent application in the name of QUEST INTERNATIONAL (WO 96/26266) have nitrogenous material contents of, respectively, 54% for the soybean extracts, 75% for the wheat extracts and 69% for the rice extracts.

The present invention therefore differs from the prior art by virtue of the high content of nitrogenous material of the peptide extract used.

In addition, it has also been demonstrated by the inventors that said nitrogenous material comprises few free amino acids, but consist mainly of very small peptides. For the protocols and results, reference should be made to the examples hereinafter.

More particularly, the use according to the invention is characterized in that said nitrogenous material consists of approximately 50% to approximately 60% of peptides having a molecular size of less than 500 daltons.

It is generally accepted that peptides of less than 500 daltons are mainly in the form of di-, tri-, tetra- or pentapeptides. In fact, the average molar mass of amino acids is approximately 150 g/mol, with the lowest corresponding to 75.1 g/mol for glycine and the highest to 204.2 g/mol for tryptophan.

According to a further aspect of the invention, the use is characterized in that said nitrogenous material consists of approximately 20% to approximately 30% of peptides having a molecular size of between 500 and 1000 daltons.

Still in the interests of characterizing the peptide extract which is the subject of the present invention, it has been demonstrated that said extract has a high content of acidic amino acids.

More particularly, the present invention therefore relates to the use as described above, characterized in that said extract comprises between 20 and 40 mol % of aspartic acid and of glutamic acid and/or of their respective amides.

Finally, the invention is characterized in that said peptide extract comprises less than 1% by mass of phenolic compounds.

More particularly, said peptide extract has the following total amino acid composition:

| Amino acids | mol % |
| --- | --- |
| Alanine | 2-6 |
| Arginine | 5-9 |
| Aspartic acid + asparagine | 10-14 |
| Cysteine | 0 |
| Glutamic acid + glutamine | 15-19 |
| Glycine | 7-11 |
| Histidine | 1-5 |
| Isoleucine | 2-6 |

-continued

| Amino acids | mol % |
| --- | --- |
| Leucine | 5-9 |
| Lysine | 2-6 |
| Methionine | 0-3 |
| Phenylalanine | 1-5 |
| Proline | 3-7 |
| Serine | 5-9 |
| Threonine | 5-9 |
| Tryptophan | not determined |
| Tyrosine | 1-5 |
| Valine | 5-9 |

The percentages indicated in the table above consist of averages, of which the methods of measurement are clearly detailed in the examples. Various preferred concentrations will also be illustrated in the same examples.

According to a preferred embodiment, the use according to the invention is characterized in that said cells consist of eukaryotic cells, preferably animal cells.

By way of nonlimiting example of preferred eukaryotic cells, mention may be made of the cells used in the industry, for instance CHO, BHK, NS0, PER C6, VERO, HEK293, etc. cells.

According to another aspect, the present invention is not limited to the use of a peptide extract as described above as supplementation element, but it also relates to a serum-free culture medium.

More particularly, the present invention is directed toward a serum-free cell or tissue culture medium obtained by using, or comprising, a peptide extract as described above.

As mentioned above, the culture media preferably consist of a "basal" medium selected according to the type of culture desired, to which are added sera or else supplements such as hydrolyzates. The culture medium that is the subject of the present invention is distinguished by the very nature of the extract added, i.e. an extract derived from oil-yielding plants, more particularly from rapeseeds, as described above.

The "basic" media used therefore depend on the nature of the desired culture. By way of nonlimiting examples, mention may be made of the following media: RPMI (Roswell Park Memorial Institute), MEM (Minimum Essential Medium), Iscove's, IMDM (Iscove's Modified Dulbecco's medium), Ham's, NCTC, TC100, Grace, etc.

In practice, the extracts according to the invention are used in the form of solutions in which the concentrations of these same peptide extracts can vary according to the type of culture desired. By way of nonlimiting example, in the case of a culture of CHO (Chinese hamster ovary) type cells, the preferred concentrations are of the order of from 2 to 6 g/l, preferably 4 g/l. As will emerge from the examples hereinafter, a lower concentration is not sufficient and a higher concentration leads to an inhibition of cell growth or potentially cell apoptosis.

For the examples hereinafter, the reference medium used is RPMI 1640 medium (SIGMA-ALDRICH).

According to one embodiment, the culture medium according to the invention is characterized in that it also comprises vitamins, inorganic salts, free amino acids, organic acids and/or sugars.

The present invention also covers the use of a culture medium according to the present invention, for the bulk culturing of cells or tissues.

According to another aspect of the present invention, a culture medium that is not only serum-free, but also protein-free, i.e., as explained above, devoid of animal proteins, is also covered.

A subject of the present invention is also a protein-free cell or tissue culture medium obtained by using, or comprising, a peptide extract as described above.

In a manner similar to that which has been described above for the serum-free media, according to one embodiment, the protein-free culture medium according to the invention can also comprise vitamins, inorganic salts, free amino acids, organic acids and/or sugars.

The invention also covers the use of a protein-free culture medium according to the present invention, for the bulk culturing of cells or tissues.

According to another embodiment, the present invention relates to a method of in vitro cell or tissue culture. As regards the actual steps of the method, mention may be made, by way of nonlimiting example, of i) static-mode culturing on a very small scale (96-well plates), ii) static-mode culturing on slightly larger scales (25 cm$^2$, 75 cm$^2$ and 175 cm$^2$ culture flasks), then iii) agitated-mode culturing on increasing scales (Erlenmeyer flasks, spinners and cell cultivators that are controlled). More particularly, the seeding can be carried out by any conventional technique known to those skilled in the art.

More particularly, the present invention is directed toward a method of in vitro cell or tissue culture in a medium devoid of serum, characterized in that it consists in seeding said cells or tissues into a medium comprising a peptide extract obtained by successive fractionations of a plant starting material, said plant starting material consisting of rapeseed.

One embodiment consists in carrying out the fractionation process described above so as to obtain an extract having the listed properties.

More particularly, the method according to the invention is characterized in that said starting material consists of rapeseed cake.

Even more particularly, the method according to the invention is characterized in that said extract consists of at least 80%, preferably at least 90%, by mass of nitrogenous material.

More particularly, the method according to the invention is characterized in that said nitrogenous material consists of approximately 50% to approximately 60% of peptides having a molecular size of less than 500 daltons.

Even more particularly, the method according to the invention is characterized in that said nitrogenous material consists of approximately 20% to approximately 30% of peptides having a molecular size of between 500 and 1000 daltons.

Preferably, the method according to the invention is characterized in that said extract comprises between 20 and 40 mol % of aspartic acid and of glutamic acid and/or of their respective amides.

Finally, even more preferably, the method according to the invention is characterized in that said extract has the following total amino acid composition:

| Amino acids | mol % |
| --- | --- |
| Alanine | 2-6 |
| Arginine | 5-9 |
| Aspartic acid + asparagine | 10-14 |
| Cysteine | 0 |
| Glutamic acid + glutamine | 15-19 |
| Glycine | 7-11 |
| Histidine | 1-5 |
| Isoleucine | 2-6 |
| Leucine | 5-9 |
| Lysine | 2-6 |
| Methionine | 0-3 |
| Phenylalanine | 1-5 |
| Proline | 3-7 |
| Serine | 5-9 |
| Threonine | 5-9 |
| Tryptophan | not determined |
| Tyrosine | 1-5 |
| Valine | 5-9 |

In a manner similar to the culture media as described above, another aspect of the invention concerns a method of in vitro cell or tissue culture, said method being characterized in that it is in a protein-free medium.

More particularly, the method of in vitro cell or tissue culture in a protein-free medium is characterized in that it consists in seeding said cells or tissues into a medium comprising a peptide extract obtained by successive fractionations of a plant starting material, said plant starting material consisting of rapeseed.

In a manner similar to the method of culture in a serum-free medium, the present method of culture in a protein-free medium is characterized in that said starting material consists of rapeseed cake.

More particularly, the method according to the invention is characterized in that said extract consists of at least 80%, preferably at least 90%, by mass of nitrogenous material.

Even more particularly, the method according to the invention is characterized in that said nitrogenous material consists of approximately 50% to approximately 60% of peptides having a molecular size of less than 500 daltons.

Preferably, the method according to the invention is characterized in that said nitrogenous material consists of approximately 20% to approximately 30% of peptides having a molecular size of between 500 and 1000 daltons.

Even more preferably, the method according to the invention is characterized in that said extract comprises between 20 and 40 mol % of aspartic acid and of glutamic acid and/or of their respective amides.

More particularly, the method according to the invention is characterized in that said extract has the following total amino acid composition:

| Amino acids | mol % |
| --- | --- |
| Alanine | 2-6 |
| Arginine | 5-9 |
| Aspartic acid + asparagine | 10-14 |
| Cysteine | 0 |
| Glutamic acid + glutamine | 15-19 |
| Glycine | 7-11 |
| Histidine | 1-5 |
| Isoleucine | 2-6 |
| Leucine | 5-9 |
| Lysine | 2-6 |
| Methionine | 0-3 |
| Phenylalanine | 1-5 |
| Proline | 3-7 |
| Serine | 5-9 |
| Threonine | 5-9 |
| Tryptophan | not determined |
| Tyrosine | 1-5 |
| Valine | 5-9 |

Finally, according to a last aspect of the present invention, particularly advantageous properties have been demonstrated with regard to the adapation of a medium with serum to a medium according to the invention. In fact, it may be advantageous, for various reasons known to those skilled in the art, for instance (i) the obtaining of new cell lines by genetic modification (transfection), (ii) a higher cell viability during thawing subsequent to freezing in a medium containing serum, (iii) higher growth and (iv) greater resistance of the cells to shear forces, to start a culture in a medium with serum and, more or less rapidly, to switch this culture into a medium devoid of serum and/or protein-free. It is known that such transfers are difficult to implement since the cells have trouble withstanding such a change which constitutes a stress for them, which, in most cases, is fatal to them. In order to avoid such a stress, the cells are gently transferred into media comprising decreasing concentrations of serum so as to gently adapt the cells to the new serum-free medium. Such a period, referred to as adaptation period, is relatively long and tedious.

Entirely surprisingly, the inventors have shown that this stress can be avoided by transferring the cultures into a serum-free medium containing the peptide fraction that is the subject of the invention, even abruptly. This property of the invention will emerge clearly from the examples and figures hereinafter.

The present invention therefore relates to a method for directly transferring an in vitro culture in a medium with serum, to a culture in a serum-free medium, characterized in that it consists in recovering the cells and/or the tissue from the medium with serum, and in seeding them or it directly into a serum-free medium as described in the present patent application.

According to yet another advantageous aspect, the present invention relates to a method for adapting an in vitro culture in a medium with serum, to a culture in a serum-free medium, characterized in that it consists in recovering the cells and/or the tissue from the medium with serum, and in seeding them or it, stepwise, into media having decreasing serum concentrations, respectively.

The present invention covers a method of adaptation as described above, characterized in that said method of adaptation comprises the following four steps:
  step 1: 75% medium with serum/25% serum-free medium+peptide extract,
  step 2: 50% medium with serum/50% serum-free medium+peptide extract,
  step 3: 25% medium with serum/75% serum-free medium+peptide extract,
  step 4: 100% serum-free medium+peptide extract.

According to another aspect, a subject of the invention is a method for directly transferring an in vitro culture in a medium with serum, to a culture in a protein-free medium, characterized in that it consists in recovering the cells and/or the tissue from the medium with serum, and in seeding them or it directly into a protein-free medium as described in the present invention.

According to a further embodiment, the present invention covers a method for adapting an in vitro culture in a medium with serum, to a culture in a protein-free medium, characterized in that it consists in recovering the cells and/or the tissue from the medium with serum, and in seeding them or it, stepwise, into media having decreasing serum concentrations, respectively.

More particularly, the method of adaptation according to the invention is characterized in that said method of adaptation comprises the following four steps:
  step 1: 75% medium with serum/25% serum-free medium+peptide extract,
  step 2: 50% medium with serum/50% serum-free medium+peptide extract,
  step 3: 25% medium with serum/75% serum-free medium+peptide extract,
  step 4: 100% serum-free medium+peptide extract.

Finally, according to a last aspect, a subject of the present invention is a method for adapting an in vitro culture in a medium with serum, to a culture in a protein-free medium, characterized in that said method comprises the following steps:
  step 1: carrying out the method that is the subject of the invention,
  step 2: recovering the cells and/or the tissues from the serum-free medium,
  step 3: seeding said cells and/or tissues directly into a protein-free medium.

The advantages of the present invention will be demonstrated in the light of the examples and figures hereinafter, in which.

EXAMPLE 1

Protocols for the Method for Generating the Peptide Extract which is the Subject of the Invention The protocol described hereinafter is illustrated by FIG. 1. More particularly, the present example reiterates all the steps, providing details of them, according to one of the preferred embodiments. It is clearly understood that variations, obvious to those skilled in the art, may be introduced into this method.

Step 1: Protocol for Rapeseed Protein Extraction

The protocol followed for this step is represented in the scheme below.

The plant proteins used are a deoiled industrial meal, which is a residue from the oil industry (Novance, Compiègne, France), containing 35% by weight of nitrogenous material. Starting from this substrate, a protein concentrate is prepared (75% of nitrogenous material) by extraction with sodium hydroxide and acid precipitation at the isoelectric pH of the proteins (pH 4).

The total yield of proteins from the method for obtaining the concentrate from the rapeseed cake is approximately 28%.

The composition of the concentrate obtained is the following (see Table 1).

TABLE 1

Composition of the concentrate obtained

|  | Proteins | Fiber | Lipids | Ash | Others |
|---|---|---|---|---|---|
| Content (%) | 75 | 14 | 5 | 3 | 3 |

Step 2: Protocol for Hydrolysis of the Rapeseed Cake Protein Concentrate

Use of Alcalase 2.4 L®, which is an enzyme preparation of microbial origin, at an enzyme concentration/substrate concentration ratio=1/10.

The concentrate is hydrolyzed enzymatically in a thermostated (60° C.) stirred reactor, through the action of Alcalase 2.4 L® (NovoNordisk, Bagsvaerd, Denmark), with pH regulation (pH 9 maintained by adding sodium hydroxide). After 5 hours of hydrolysis, corresponding to a degree of hydrolysis of 28% (pH-stat technique), the reaction is stopped by inactivation of the enzyme (90° C. for 10 min).

Step 3: Acid Precipitation, pH 4

The pH of the hydrolyzate obtained at the end of step 2 is then lowered to 4 in order to precipitate the large molecules and concentrate the peptides in the supernatant. This new step makes it possible to eliminate the large molecules responsible for clogging during the subsequent filtration steps, and to concentrate the relatively small peptides.

Step 4: Ultrafiltration with a Membrane Having a Cutoff Threshold of 3 kDa

The objective of this step is to purify the small peptides by eliminating the molecules greater than 3000 Da in size (phenolic compounds+polypeptides).

The process uses a conventional regenerated cellulose membrane for concentrating the peptides of theoretical molar mass less than 3000 g/mol.

Step 5: Nanofiltration with a Membrane Having a Cutoff Threshold of 500 Da

The objective of this step is to decrease the amount of free amino acids in the small-peptide solution obtained after step 4, and to desalify this same solution in order to reduce the osmolarity of the mixture.

This separation step, which involves a membrane consisting of a polyamide/polysulfone composite film, results in an 80% reduction in the salt concentration, thereby allowing better fractionation of the peptides according to their charge in the following step 6.

Step 6: Ultrafiltration with a Membrane Having a Cutoff Threshold of 1 kDa

The objective is to fractionate the small peptides according to their size and their charge.

A conventional regenerated cellulose membrane is used with the aim of fractionating, according to their size but also according to their charge, as a function of the conditions under which the membrane is used, the peptides recovered after step 5, the molar masses of which should theoretically be between 500 and 3000 g/mol.

The realization of this step produces two fractions:
 a permeate containing essentially peptides of molar mass theoretically less than 1000 g/mol,
 a retentate which, compared to the permeate, has, firstly, a higher content of peptides containing acidic amino acids and, secondly, a lower content of peptides containing basic amino acids.

The peptide extract that is the subject of the present invention consists of the retentate obtained by carrying out the method as described above.

Modifications can obviously be introduced. By way of nonlimiting example, it is possible to envision adjusting the pH to 4 during steps 5 and 6, instead of 9, or alternatively eliminating step 5.

EXAMPLE 2

Protocols Implemented for Characterizing the Extract that is the Subject of the Invention 2.1 Assaying Nitrogen by the Kjeldahl Method Reagents Mineralization catalyst (17% $Na_2SO_4$; 1.5% $CuSO_4.5H_2O$; 1.5% salts): Prolabo, 22550-293

1N H$_2$SO$_4$: Labosi A4715891
35% H$_2$O$_2$: Labosi, A4823251
40% NaOH: Merck, 191537
H$_3$BO$_3$: Labosi, A4703851

Material

Vapodest 4 titramatic automatic Kjeldahl apparatus: Gerhardt GmbH & Co. KG, Bonn, Germany.
645 Multi-dosimat automatic titration system: Metrohm, Herisau, Switzerland.
Kjeldatherm® KT 12 S mineralization block: Gerhardt GmbH & Co. KG, Bonn, Germany.

Assay Protocol

The protein content was determined by the Kjeldahl method. This assay method is based on the conversion of organic nitrogen to inorganic nitrogen in the form of ammonium sulfate (NH$_4$)$_2$SO$_4$. The assay is carried out automatically with the Vapodest 4S. For each sample, the analysis is performed twice so as to be able to calculate an average value. It is also necessary to perform an assay on a blank, in order to obtain, after subtraction, a value for the total nitrogen really contained in the sample.

The results are expressed as nitrogen concentration by mass, according to the formula: amount of nitrogen $$(g/l) = (V - V_0) \times N \times 14 / E$$

with V: volume of H$_2$SO$_4$ required to titrate the sample, in ml,
V$_0$: volume of H$_2$SO$_4$ required to titrate the blank, in ml,
N: H$_2$SO$_4$ solution titer (mol/l),
E: sample size in mg or in ml.

The protein percentage is obtained by means of the conversion coefficient for rapeseed proteins (6.25), itself calculated from the nitrogen content of these proteins (16%): amount of proteins=6.25×amount of nitrogen. It emerges from this calculation that the % protein of the extract which is the subject of the invention is approximately 90% (see Table 2 hereinafter).

2.2. Acid Hydrolysis of Peptides and Assaying of Amino Acids

Reagents
trichloroacetic acid at 50% (w/v) in water: Prolabo, 20734.295
9-fluorenylmethyl chloroformate (FMOC-Cl): OSI, A4 700.792,
2.5 mg/ml in acetonitrile: Fluka, 23184
o-phthalaldehyde (OPA): Fluka, 79760
3-mercaptopropionic acid (3-MPA): Sigma, M-6750
10 mg of each of the compounds (OPA and 3-MPA) in 1 ml of 0.4 N borate buffer, pH 10.5: Hewlett-Packard, 5061-3339
standard solution of a mixture of amino acids: Sigma, AA-S-18
2N NaOH solution: Fluka, 72071
6N HCl: Labosi, A4715801

Eluting Solutions:
Solvent A: 20 mM of sodium acetate. 3H$_2$O (OSI, 27652.298), containing 0.024% (v/v) of triethylamine (OSI, 28 745.296) and 0.5% (v/v) of tetrahydrofuran (OSI, 28 556.293). The mixture is adjusted to pH 7.2 with acetic acid (OSI, 20 104.298).
Solvent B: 20% (v/v) of a 100 mM sodium acetate buffer (OSI, 27 652.298) adjusted to pH 7.2 with acetic acid, 40% (v/v) of acetonitrile and 40% (v/v) of methanol (Prolabo, 20 865.322).

Material
0.22 μm single-use filters: Schleicher & Schuell, Dassel, Germany
incubator model 700: Memmert, Schwabach, Germany
Hypersil C18 column: Interchim, H5 C18-20R, Montluçon, France
HP 1090 chromatography system: Hewlett Packard, Palo Alto, United States.

Method

An acid hydrolysis of the peptide fractions is carried out beforehand in order to obtain a homogeneous mixture of free amino acids. A sample of 1 g or of 1 ml is placed in a stoppered test tube. 4 ml of hydrochloric acid (6 N) are then added and the test tube is then placed in a nitrogen atmosphere before being hermetically closed. The hydrolysis is then carried out in an incubator at 110° C. for 24 h. After cooling, the hydrolyzates are neutralized to a pH of approximately 6 by adding 4N sodium hydroxide. The samples are finally filtered through a 0.22 μm syringe filter.

The disadvantage of acid hydrolysis is the destruction of the tryptophan and the conversion of glutamine and asparagine to glutamic acid and aspartic acid, respectively. The tryptophan analysis can be carried out after an alkaline hydrolysis, by ion exchange chromatography (Hugli T. E. et al., 1972, Determination of the tryptophan content of proteins by ion exchange chromatography of alkaline hydrolysates, Ibid., 247, 2828-2834). Given that the amount of tryptophan is very limited in rapeseed (Godon B., 1996, Les méthodes courantes de laboratoire pour la séparation et l'analyse des protéines végétales [Current laboratory methods for the separation and analysis of plant proteins]. In: publisher Lavoisier. Protéines végétales [Plant proteins], 65-80), this amino acid is not analyzed. As regards the glutamine and asparagine, their quantification will be integrated with the corresponding acidic amino acids, in the forms Glx and Asx (Glx=Gln+Glu, Asx=Asn+Asp).

Protocol

The amino acids and the alanyl-glutamine and glycyl-glutamine dipeptides are assayed by reverse-phase liquid chromatography after derivatization in the presence of o-phthalaldehyde (QPA) and 9-fluorenyl-methyl chloroformate (FMOC). The principle of the derivatization is the following: the primary amino acids are placed in the presence of OPA and 3-mercapto-propionic acid (3-MPA), to give isoindoles that are highly fluorescent and absorbent in the UV range (338 nm) (Godel et al., 1992, Automated amino acid analysis using combined OPA and FMOC-Cl precolumn derivatization, LC-GC INTL., 5, 44-49).

According to the same principle, the secondary amino acids are derivatized in the presence of FMOC, to give derivatives that are highly fluorescent and absorbent in the UV range (262 nm). The detection threshold is of the order of 100 pmol.

The samples are automatically derivatized using a Hewlett Packard HP 1090 liquid chromatograph system. 3 μl of sample are first of all neutralized with 1.5 μl of 2 N NaOH, in order to obtain complete derivatization. The whole is then mixed with 6.0 μl of 0.4 N borate buffer, 2.5 μl of the solution of OPA+3-MPA and 2.5 μl of the FMOC solution. The mixing lasts 15 min in order to allow the derivatization; finally, the whole is injected onto the Hypersil C18 separating column. The eluting solvent is composed of 100% solution A for 17 min, then of 40% of solution A and 60% of solution B for 1 min and, finally, of 100% of solution B for 7 min. The amino acids are separated according to their polarity; the most polar come off the column at the beginning of analysis and the least polar at the end of analysis. As they come off the column, the primary amino acids and the dipeptides are detected by means of a UV detector at 338 nm, and the secondary amino acids are detected by means of a UV detector at 262 nm. The total analysis time is 25 min.

The determination of the amount of free amino acids is carried out according to the same protocol, except for the absence of an acid hydrolysis step.

Before sample analysis, three solutions, containing 17 amino acids at concentrations of 0.25, 0.5 and 2.5 mM respectively, are derivatized and injected without prior neutralization with 2 N NaOH. The profiles obtained serve to establish a standard range for each amino acid, which then makes it possible to determine the concentration of each amino acid contained in a sample after integration of the peaks (Hewlett Packard system).

2.3. Assaying of the Solids

The water content was determined by bringing the samples (1 to 5 g) to 105° C. in an incubator until a constant mass was obtained.

2.4. Determination of the Size of the Peptides by Size Exclusion Chromatography

Material

Superdex peptide HR 10/30 column (7000-200 Da): Amersham Biosciences, Uppsala, Sweden 0.22 µm Minisart RC 25 filters: Sartorius, Goettingen, Germany vacuum filtration device, sintered glass funnel SM 16309: Sartorius, Goettingen, Germany BioCAD® 700$^E$ chromatography system: Applied Biosystems, Foster City, United States fraction collector model 203B: Gilson, Middleton, United States.

Method

The operating conditions are the following:

eluent: ACN/H$_2$O/TFA (40/60/0.1-v/v/v), filtered through 0.45 µm solvent degassed with helium: 5 ml/min eluent flow rate: 0.6 ml/min column temperature: ambient (25° C.)

detection: UV at 214 nm injected volume: 50 µl analysis time: 45 min

The column was pre-calibrated with peptides of known molar masses. Two straight lines were obtained by plotting the logarithm of the molar mass as a function of the retention time. The determination of the relationship linking the molar mass (MM) of the molecules to their retention time on the column made it possible to define the distribution according to the size of the peptides contained in the various fractions.

2.5. Assaying the Phenolic Compounds

The amount of phenolic compounds in the fractions was estimated as sinapic acid equivalent. Sinapic acid (Sigma, D 7927), with a molar mass of 224 g/mol, was used as reference because it is the phenolic acid predominantly present in the rapeseed cake (between 70 and 90%) according to Naczk M. et al., 1992, Recovery of rapeseed tannins by various solvent systems, Food Chem., 45, 51-54.

The calibration and the measurements were carried out using the same chromatographic conditions as those used in size-exclusion HPLC, except for the detection wavelength fixed, in this case, at 310 nm, which corresponds to the maximum absorption wavelength for this acid (Sakakibara H. et al., 2003, Simultaneous determination of all polyphenols in vegetables, fruits and teas, J. Agric. Food Chem., 51, 571-581). The amount of phenolic compounds in each fraction was expressed in mg of sinapic acid equivalents/100 g of solids. The content of free phenolic compounds was estimated by calculating the proportion of the area under the peak having a retention time (between 34 and 37 min) identical to that of the standard used to establish the calibration curve.

The results of Example 2 are given in the tables below:
Composition of the Nitrogenous and Phenolic Material of the Peptide Extract:
(see Table 2)

TABLE 2

|  | Peptide content | % free amino acids/PM | Amount of polyphenols (mg/100 g S) |
|---|---|---|---|
| Extract | 90% | 3% | 31% tannins<br>65% bound phenolic acids<br>4% free phenolic acids |

PM: peptide material;
S: solids.

Peptide Size Distribution (Relative to Total Peptide Material):
(see Table 3)

TABLE 3

|  | Size (Da) | | | |
|---|---|---|---|---|
|  | >5000 | 5000-1000 | 1000-500 | <500 |
| Extract | 0% | 20% | 23% | 57% |

Amino Acid Composition of the Peptide Extract (3 Analyses):
(see Table 4)

TABLE 4

| aa | % | % | % |
|---|---|---|---|
| Asx | 13 | 12 | 12 |
| Glx | 17 | 17 | 20 |
| Ser | 7 | 7 | 5 |
| His | 3 | 3 | 2 |
| Gly | 9 | 9 | 9 |
| Thr | 7 | 7 | 5 |
| Ala | 4 | 4 | 5 |
| Arg | 7 | 7 | 7 |
| Tyr | 2 | 3 | 3 |
| Cys | 0 | 0 | 0 |
| Val | 7 | 7 | 8 |
| Met | 1 | 1 | 0 |
| Phe | 3 | 3 | 3 |
| Ile | 4 | 4 | 4 |
| Leu | 7 | 7 | 7 |
| Lys | 4 | 4 | 4 |
| Pro | 5 | 5 | 6 |
|  | 100 | 100 | 100 |

Asx: aspartic acid + asparagine
Glx: glutamic acid + glutamine

In all of Examples 4 to 9 hereinafter, and unless otherwise indicated in the text, the cultures were carried out with CHO-C5 cells in the following culture media:
Reference medium (○)=RPMI 1640 (Sigma)+BITS+ET+glutamine
Medium of interest (Δ)=reference medium+4 g/l of peptide extract according to the invention.

EXAMPLE 3

Effect of a Sterilizing Filtration

The culture system used consists of a 125 ml Erlenmeyer flask, Vu=25 ml.

CHO-C5 cells were cultured in reference medium (○) or in medium of interest (Δ) sterilized once ((open symbols) or 3 times (solid symbols) by 0.22 µm sterilizing filtration.

Figure 2:
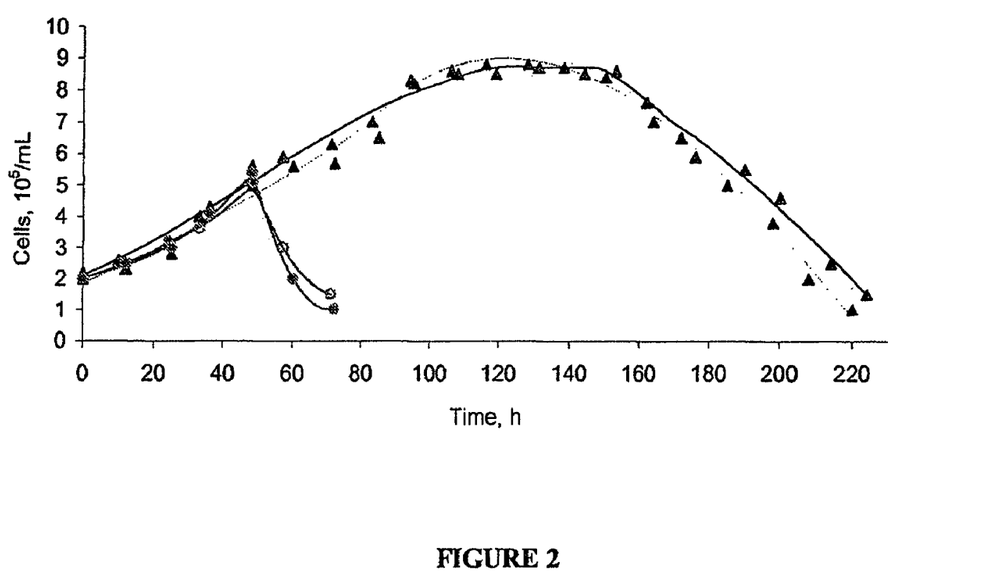
FIG. 2 represents the effect of a sterilizing filtration on the extract according to the invention.

The results obtained are represented in FIG. 2.

It emerges from the latter that there is no decrease in the effect of the peptide extract according to the invention when 0.22 μm filtration is carried out.

EXAMPLE 4

"Cryoprotective" Effect of the Peptide Extract According to the Invention (see Table 5)

The culture system used consists of static culture flasks.

TABLE 5

| | | Duration of storage period at −196° C. | | | | | | | | | | | |
|---|---|---|---|---|---|---|---|---|---|---|---|---|---|
| | | 1 week | | | | 1 month | | | | 5 months | | | |
| | | Time after thawing and placing in culture again (h) | | | | | | | | | | | |
| | | 0 | 24 | 48 | 96 | 0 | 24 | 48 | 96 | 0 | 24 | 48 | 96 | 120 |
| % viability | Reference M. | 61 | 44 | 60 | 81 | 46 | 33 | 36 | 65 | 44 | 34 | 36 | 53 | 72 |
| | M of interest | 64 | 52 | 56 | 85 | 58 | 46 | 55 | 74 | 39 | 38 | 45 | 68 | 92 |

A better recovery of the cells frozen in the presence of the extract according to the invention is observed. This property is particularly advantageous in the sense that, in practice, the cells are often frozen and then thawed in order to be, for example, conserved or else transported.

EXAMPLE 5

Effect of the Concentration of the Extract According to the Invention on Maximum Cell Density The culture system used consists of 96-well plates, Vu=200 μl. The growth was followed with the Cellscreen apparatus (Innovatis).

Figure 3:
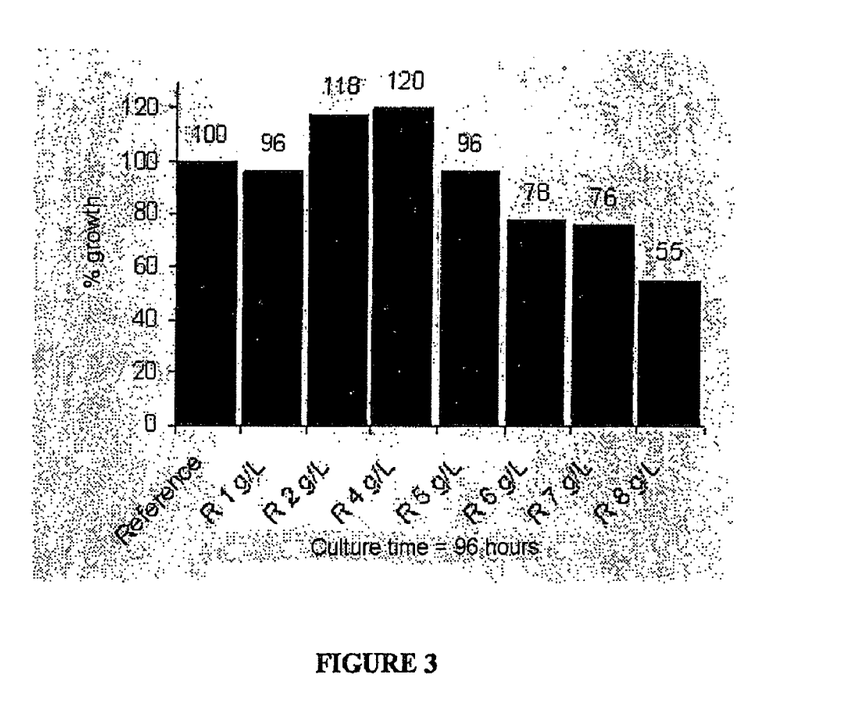
FIG. 3 represents, in the form of a histogram, the effect of the concentration of the extract according to the invention on the maximum cell density.

The results obtained are given in FIG. 3.

These results show that the concentration of 4 g/l is the one that provides the best results. Concentrations that are too high compromise the growth. Without wishing to be bound by any theory, the inventors put forward the hypothesis that the concentration of inhibitors or of toxic compounds could destroy the positive effect of the activators.

EXAMPLE 6

Assays Relating to Adaptation of Various Cells 6.1. Switching a Medium with 10% of Serum to a Serum-Free Medium Containing the Extract According to the Invention The culture system used consists of static culture flasks.
6.1.1. VERO Cells (Adherent Cells)

Figure 4:
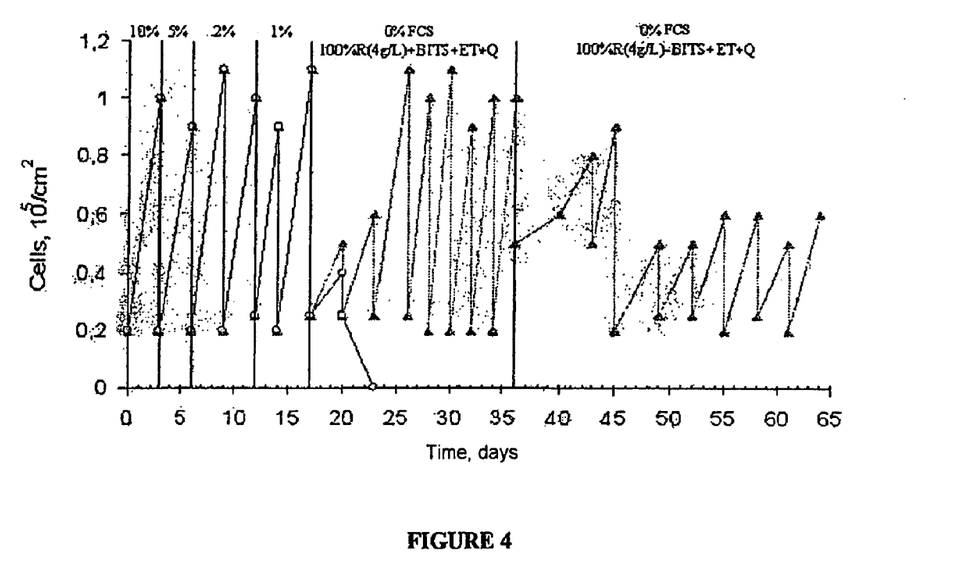
FIG. 4 illustrates the adaptation of VERO cells from a medium with serum, to a serum-free medium and to a protein-free medium comprising the extract according to the invention.

The basic medium used is αMEM. The adaptation carried out is an abrupt adaptation. The results obtained are represented in FIG. 4.

The successive passages of VERO cells, illustrated by the curve (Δ), represent the adaptation in the presence of extract according to the invention. The curve (○) represents the adaptation of the cells in the absence of extract. From D0 to D17, the FCS is decreased from 10 to 1%. At D17, the FCS is abruptly eliminated and replaced with the mixture (peptide extract according to the invention, BITS, ET, Q). At D36, the BITS are eliminated.

It emerges from the results obtained that, in the absence of peptide extract in accordance with the invention, the adaptation is impossible (the cells are dead within two passages). In the presence of said extract and of BITS, the adaptation of the cells is rapid (recovery of growth at the $3^{rd}$ passage). In the presence of this same extract and in the absence of animal proteins (protein-free medium), the adaptation is slightly more difficult, but remains possible.

In the presence of BITS and of peptide extract and in the absence of serum, the VERO cells remain adherent. When the BITS are removed, these cells also remain adherent, but to a lesser degree (the time required for trypsinization is greatly decreased).
6.1.2. Hybridomas (Cells in Suspension)

The basic medium used is RPMI.
Abrupt Adaptation

Figure 5:
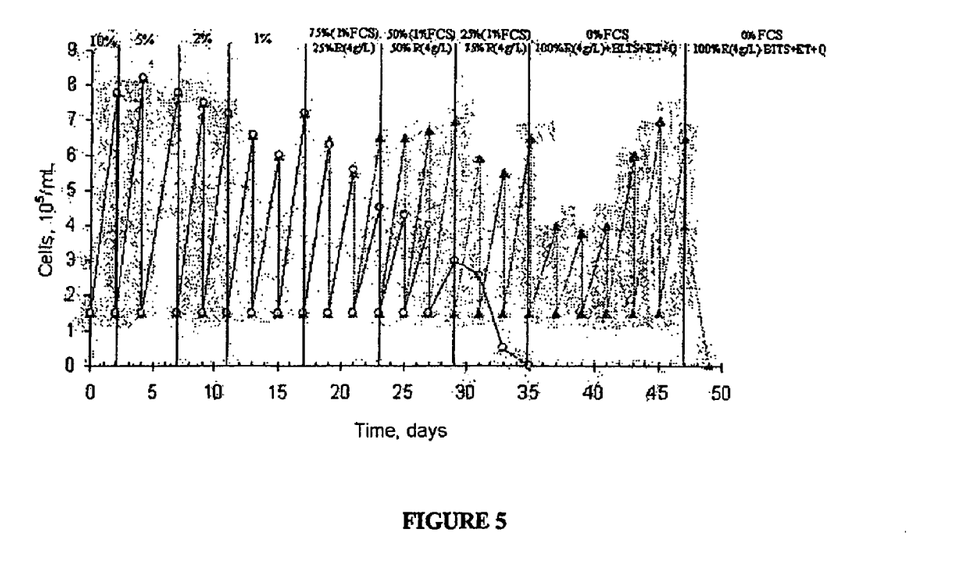
FIG. 5 illustrates the adaptation of hybridoma-type cells from a medium with serum, to a serum-free medium comprising the extract according to the invention.

In the case of an abrupt adaptation, the death of the cells is rapidly observed when the FCS is abruptly substituted with the mixture (peptide extract+BITS+ET+Q).
Gentle Adaptation Successive passages of hybridoma cells were carried out. The results obtained are illustrated in FIG. 5, in which the curve (Δ) represents the adaptation in the presence of extract according to the invention and the curve (○) represents the adaptation of the cells in the absence of extract according to the invention. From D0 to D17, the FCS is decreased from 10 to 1%. From D17 to D35, the FCS is gradually eliminated and replaced with the mixture (peptide extract, BITS, ET, Q). At D47, the BITS are eliminated.

The results obtained show that, in the absence of peptide extract, the adaptation is impossible (the cells are dead within 2 passages in the 25%/75% mixture). In the presence of extract and of BITS and in the absence of serum, the hybridomas adapt correctly (recovery at the $4^{th}$ passage). Elimination of the animal proteins (BITS) leads to instantaneous death of the cells.
6.1.3. CHO K1 dhfr⁻ (CHO DUXB11) (Cells in Suspension)

The basic medium used is αMEM+ribo- and deoxyribonucleosides.
Abrupt Adaptation

Figure 6:
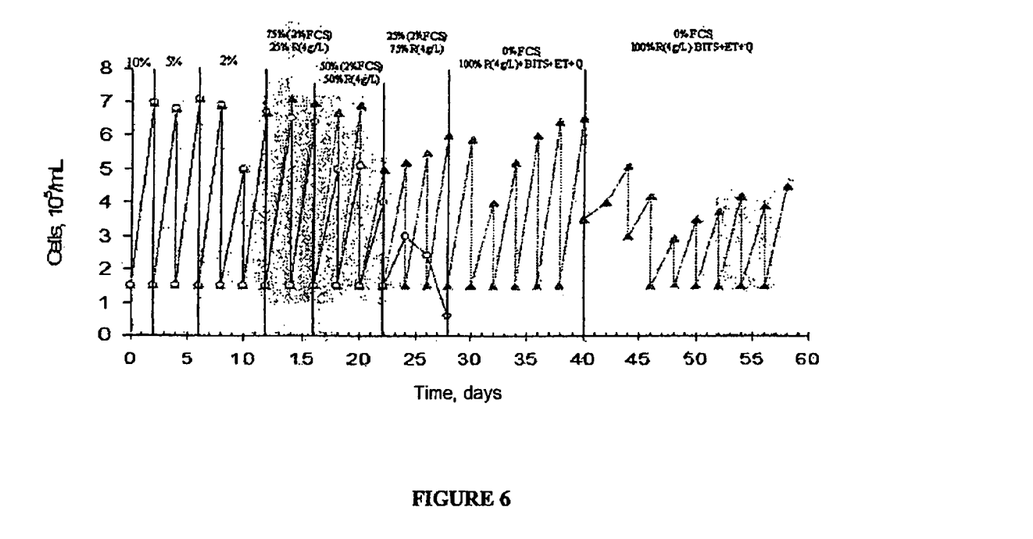
FIG. 6 illustrates the adaptation of CHO K1 dhfr⁻ cells from a medium with serum, to a serum-free medium and to a protein-free medium comprising the extract according to the invention.

The same observations as with the hybridoma cells are reported (data not shown).
Gentle Adaptation Several successive passages of CHO K1 dhfr⁻ cells were carried out. The results obtained are represented in FIG. 6, in which the curve (Δ) represents the adaptation in the presence of peptide extract, whereas the curve (○) represents the adaptation of the cells in the absence of peptide extract. From D0 to D12, the FCS is decreased from 10 to 2%. From D12 to D40, the FCS is gradually eliminated and replaced with the mixture (peptide extract, BITS, ET, Q). At D40, the BITS are eliminated.

It emerges from these results that, in the absence of peptide extract, the adaptation is impossible (the cells are dead within 3 passages in the 25%/75% mixture). In the presence of peptide extract and of BITS and in the absence of serum, the CHO K1 cells adapt correctly (recovery at the $1^{st}$ passage). Elimination of the animal proteins (BITS) leads to a slowing down of growth and a longer adaptation (approximately 6 passages), but said adaptation remains possible.

6.2. Shifting from a (Reference) Serum-Free Medium to a Serum-Free Medium with Peptide Extract (Medium of Interest or Medium of Interest without Protein of Animal Origin)

6.2.1. Successive Passages of CHO C5 (Cells in Suspension)

The culture system used consists of static culture flasks. Several successive passages of CHO C5 cells were carried out in reference medium (○), in medium of interest (Δ) and in medium of interest without animal proteins (x). The results obtained for the reference medium are given in FIG. 7A. The results obtained for the media of interest are, for their part, represented in FIG. 7B.

Figure 7A:
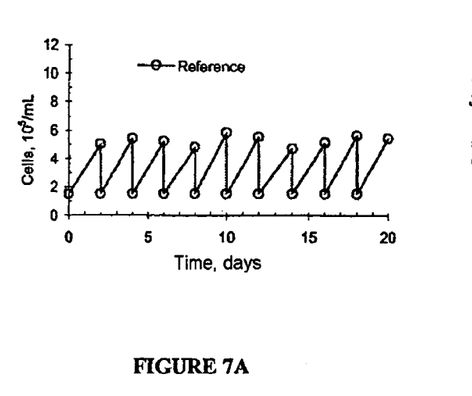
FIGS. 7A and 7B illustrate the adaptation of CHO C5 cells from a serum-free medium to a serum-free medium and to a protein-free medium comprising the extract according to the invention.
Figure 7B:
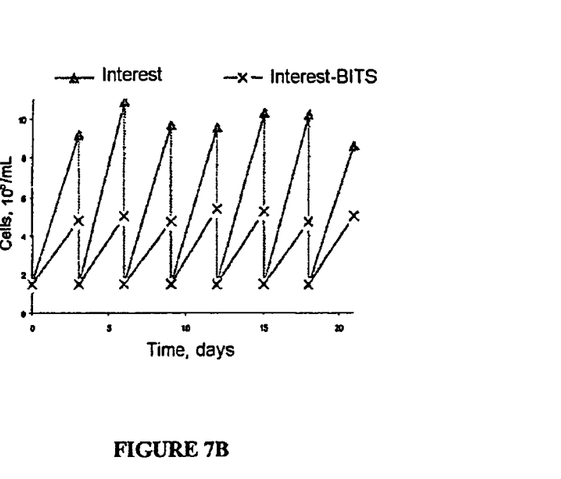

It emerges from these figures that the adaptation of the cells to the medium of interest and also the positive effect of the peptide extract are conserved for at least 7 passages. Similarly, the propagation of the cells in the medium without animal proteins makes it possible to obtain cell concentrations close to those observed in reference medium for at least 7 passages.

It may be concluded that the protein-free medium according to the invention can be used as a routine medium for maintaining the cells, all the more so since the cells can be transferred only every 3 days (instead of every 2 days for the reference medium).

6.2.2. Kinetics of Prolonged Cultures (Cells in Suspension)

The culture systems used are spinners of 500 ml, Vu=160 ml.

Figure 8:
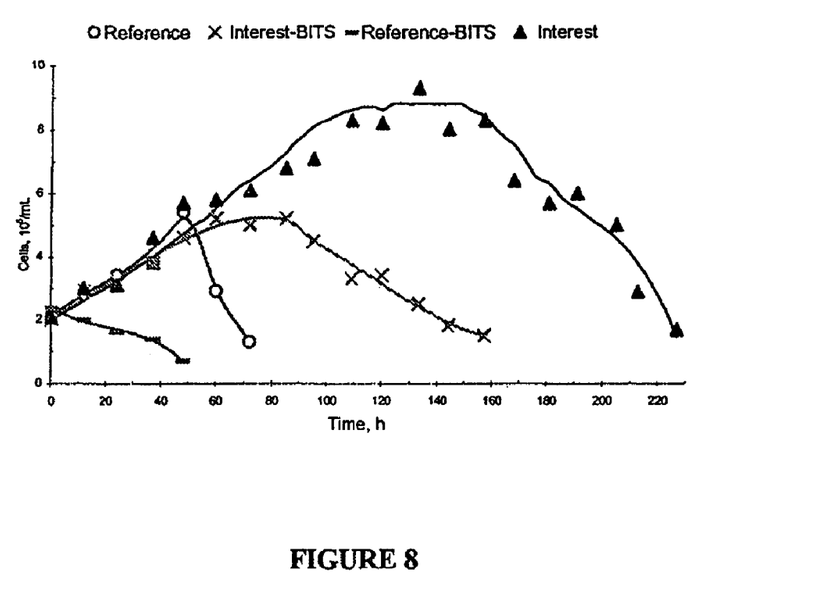
FIG. 8 represents the change in the concentration of viable cells over the course of prolonged cultures of CHO C5 cells.

The change in viable cell concentration over the course of the CHO C5 cell cultures carried out, without prior adaptation, is represented in FIG. 8. More particularly, this figure illustrates the cultures in reference medium (○), in reference medium without BITS (-), in medium of interest (Δ) and in medium of interest without BITS (x).

It clearly emerges from the results obtained that the reference medium no longer allows cell growth when the animal proteins are eliminated. The medium of interest makes it possible to virtually double the maximum concentration. Furthermore, the duration of the culture (before virtually complete disappearance of viable cells) is multiplied 3-fold.

The medium of interest allows growth when the animal proteins are eliminated. In the absence of animal proteins, and in the presence of peptide extract, the maximum cell concentration is not enhanced, but the longevity of the culture is increased by a factor 2 relative to the reference medium.

EXAMPLE 7

Effect of the Peptide Extract on the Specific Rate of Production of Interferon

The culture system used consists of a 2-liter cell cultivator, usable volume Vu=1.2 l.

Figure 9:
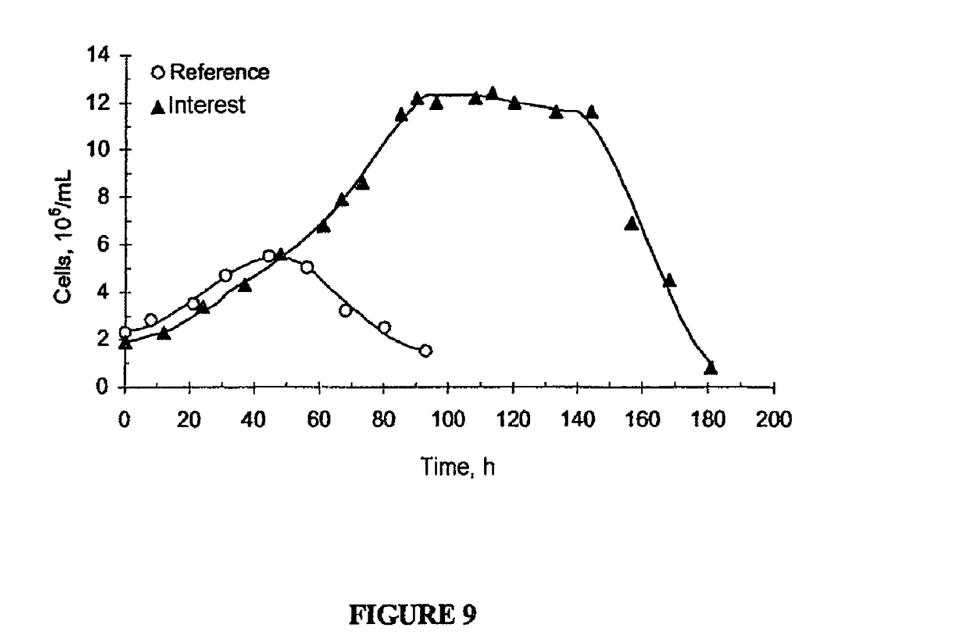
FIGS. 9, 10 and 11 illustrate the effect of the extract according to the invention on the specific rate of production of interferon by cultured CHO C5 cells.

FIG. 9 represents the growth kinetics of CHO C5 cells in reference medium (○) and in medium of interest (Δ).

Figure 10:
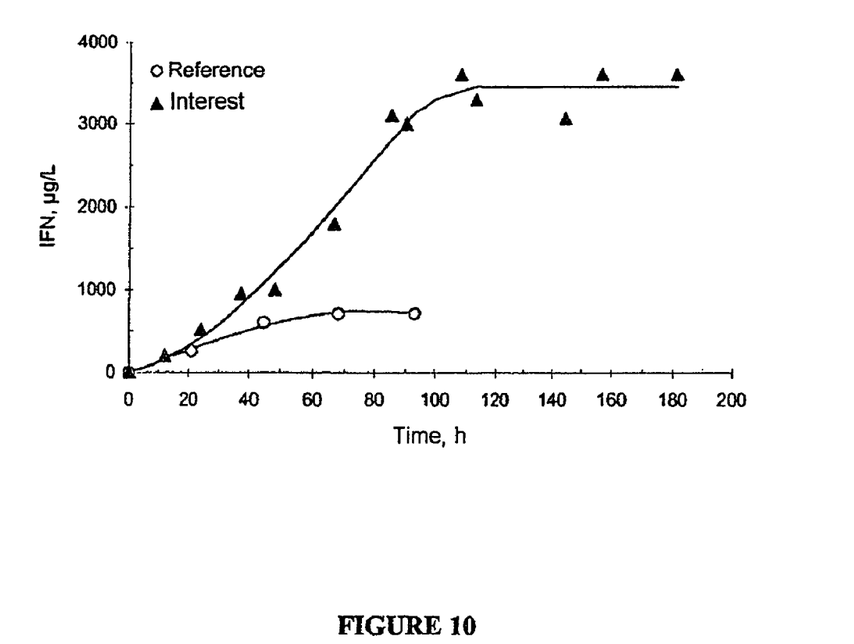

FIG. 10, for its part, represents the kinetics of IFN (gamma interferon) production by the same CHO C5 cells in reference medium (○) and in medium of interest (Δ).

Figure 11:
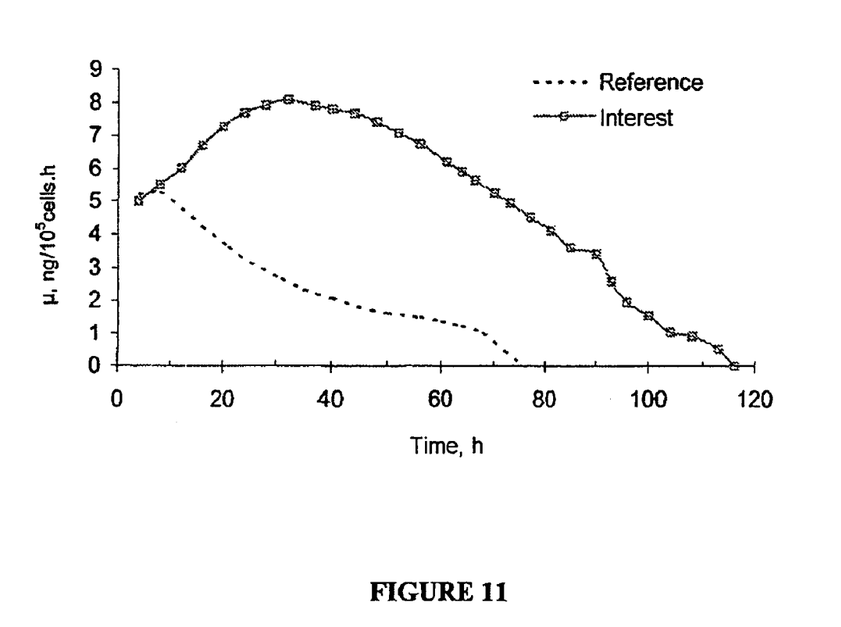

Finally, FIG. 11 illustrates the specific rate of interferon production by CHO C5 cells in reference medium (dashed line) and in medium of interest (solid line).

The positive effect of the peptide extract on the viable cells is confirmed on the reactor scale (*3.3).

A large increase in final IFN production (*5.3) is noted.

This increase may be the combined result of the increase in viable cells, but also of the increase in the specific rate of production (maximum value virtually doubled).

EXAMPLE 8

Demonstration of the Function Linked not Solely to the Elemental Amino Acid Composition, but to the Composition, of Said Amino Acids, in Peptide Form The culture system used consists of 500 ml spinners, Vu=160 ml.

Figure 12:
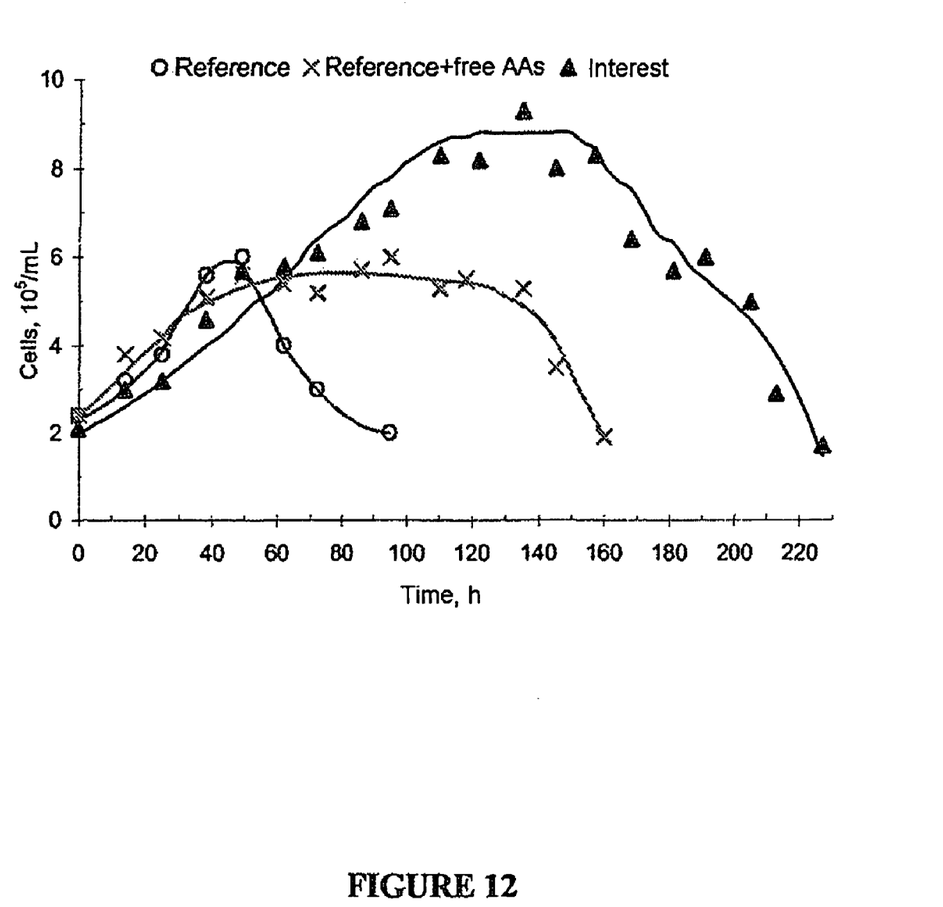
FIG. 12 demonstrates that the function of the extract according to the invention is not linked solely to the elemental amino acid composition, but to the composition, of said amino acids, in peptide form.

FIG. 12 represents the kinetics of viable CHO C5 cells cultured in spinners, in the reference medium (○), the reference medium supplemented with free amino acids (x) and the medium of interest (Δ). The free amino acids correspond to the total amino acids present in the peptide extract (peptides and free).

The addition of amino acids in the same proportion as those present in the peptide extract, in the form of peptides, does not make it possible to increase the viable cell concentration. On the other hand, a positive effect on the longevity of the culture is noted. The composition of individual amino acids, equivalent to that of the peptide mixture of the peptide extract used, contributes towards keeping the cells alive (*3 compared with the reference medium).

The peptide extract improves the amount, via a doubling of the viable cell population, but also the viability of the cells (50% additional time compared with the reference medium+ free amino acids, using the maximum cell concentration obtained in this case as reference point). These results do not appear to be solely generated by an effect linked only to the overall amino acid composition. They can also be brought about by a "growth factor" effect derived from the presence of certain peptides, with the specific composition, in the peptide extract according to the invention.

What is claimed is:

1. A method of culturing in vitro animal cells or tissues in an animal protein-free medium which comprises seeding said cells or tissues in the medium comprising a peptide extract obtained by successive fractionations of a plant starting material, wherein said plant starting material consists of rapeseed cake.

2. The method as claimed in claim 1, wherein said extract consists of at least 80%, by mass of nitrogenous material.

3. The method as claimed in claim 2, wherein said nitrogenous material consists of approximately 50% to approximately 60% of peptides having a molecular size of less than 500 daltons.

4. The method as claimed in claim 3, wherein said nitrogenous material consists of approximately 20% to approximately 30% of peptides having a molecular size of between 500 and 1000 daltons.

5. The method as claimed in claim 1, wherein said extract comprises between 20 and 40 molar % of aspartic acid and of glutamic acid and/or of their respective amides.

6. The method as claimed in claim 1, wherein said extract has the following total amino acid composition:

| Amino acids | molar % |
|---|---|
| Alanine | 2-6 |
| Arginine | 5-9 |
| Aspartic acid + asparagine | 10-14 |
| Cysteine | 0 |
| Glutamic acid + glutamine | 15-19 |
| Glycine | 7-11 |
| Histidine | 1-5 |
| Isoleucine | 2-6 |
| Leucine | 5-9 |
| Lysine | 2-6 |
| Methionine | 0-3 |
| Phenylalanine | 1-5 |
| Proline | 3-7 |
| Serine | 5-9 |
| Threonine | 5-9 |
| Tryptophan | not determined |
| Tyrosine | 1-5 |
| Valine | 5-9. |

7. The method as claimed in claim 1, wherein said extract consists of at least 90%, by mass of nitrogenous material.

* * * * *